United States Patent [19]

Geho

[11] 4,377,567
[45] Mar. 22, 1983

[54] LIPID MEMBRANE DRUG DELIVERY

[75] Inventor: Walter B. Geho, Cincinnati, Ohio

[73] Assignee: The Procter & Gamble Company, Cincinnati, Ohio

[21] Appl. No.: 75,310

[22] Filed: Sep. 13, 1979

Related U.S. Application Data

[63] Continuation-in-part of Ser. No. 948,182, Oct. 2, 1978, abandoned.

[51] Int. Cl.$^3$ ..................... A61K 43/00; A01N 25/28; A61K 9/62; B01J 13/02
[52] U.S. Cl. ...................................... 424/1; 252/316; 424/35; 424/85; 424/178; 424/DIG. 6
[58] Field of Search ...................... 252/316; 424/1, 35, 424/85, DIG. 6

[56] References Cited

U.S. PATENT DOCUMENTS 3,937,668  8/1976  Zolle .
3,957,971  11/1976  Oleniacz .

FOREIGN PATENT DOCUMENTS 830629   7/1975  Belgium .
2532317  6/1974  Fed. Rep. of Germany .
2650502  5/1978  Fed. Rep. of Germany .
2656333  6/1978  Fed. Rep. of Germany .
73/1850  of 1973 South Africa .

OTHER PUBLICATIONS

Endocrinology 90, 12 (1972)–Canfield, Kay and West.
Immunochemistry, 11, 475–481 (1974).
Lunny and Ashwell, Proc. Natl. Acad, Sci. USA, 73 341–343 (1976).
Mauk and Gamble, Proc. Natl. Acad. Sci. USA, 76, 356–369 (1979).
J. Lab. Clin. Med. 83 (4), 640–647 (1974).
FEBS Letters 62, 1, 60–63 (1976), Patel, et al.
Proceedings of the Society for Experimental Biol. and Medicine 146, 1173–1176 (1974).
Biochimica et Biophysica Acta 311, 513–544 (1974).
Gebicki, et al., Chem. Phys. Lipids 16 (2), 142–160 (1976).
New England Journal of Medicine, 9/23/76, pp. 704–710 and 9/30/76, pp. 765–770.
Journal of Lipid Research 9, 310–318 (1968).
Laboratory Investigation 34, No. 3, 276, et seq. (1976).
Proccedings of the National Academy of Sciences 71, No. 9, 3487–3491 (1974).
Life Sciences 17, 715–724.
Chem. Pharm. Bull. 23 (10) 2218–2222 (1975).
Science News, vol. 114, No. 4, (7/22/78).
Gregoriadis, Biochemical Society Transactions, vol. 3 (1975), p. 613.
Gregoriadis et al.: "Drug–Carrier Potential of Liposomes in Cancer Chemotherapy", The Lancet, Jun. 29, 1974, pp. 1313–1316.
Shipley et al.: "The Phase Behavior of Monogalactosyl, Digalactosyl, and Sulphoquinovosyl Diglycerides", Biochimica et Biophysica Acta", 311 (1973), 531–544.
Gregoriadis: "The Carrier Potential of Liposomes in Biology and Medicine", New England Journal of Medicine, Sep. 23, 1976, pp. 704–710.
Roerdink et al.: Biochimica et Biophysica Acta, 677 (1981), pp. 79–89.

Primary Examiner—Richard D. Lovering
Attorney, Agent, or Firm—Jerry J. Yetter; Steven J. Goldstein; Jack D. Schaeffer

[57] ABSTRACT

Lipid Membrane Structures comprising Digalactosyl Diglyceride target the liver of humans and lower animals and are used to carry drugs to that organ, preferentially. Digalactosyl Diglyceride LMS containing insulin provide an effective means for treating diabetes mellitus. Digalactosyl Diglyceride LMS containing interferon are used to treat viral hepatitis.

40 Claims, No Drawings

LIPID MEMBRANE DRUG DELIVERY

TECHNICAL FIELD

This application is a continuation-in-part of U.S. Patent Application, Ser. No. 948,182, filed Oct. 2, 1978, now abandoned.

The present invention relates to compositions and processes for delivering pharmacologically-active agents preferentially to the liver. More specifically, Lipid Membrane Structures ("vesicles", "liposomes") comprising digalactosyl diglyceride as a critical part of their makeup carry drug agents such as insulin preferentially to the hepatocytes of the liver.

The liver is the human body's largest gland and, as such, receives a massive blood supply through both the portal vein and the hepatic artery. Metabolically, the liver is the most complex organ in the human body and, among other multiple functions, it metabolizes/distributes drugs which are introduced into the organism. The liver is also a target organ for pharmacologically-active agents produced within the body. Accordingly, an improved means for preferentially delivering drugs to the liver provides a means for allowing the drug to be handled by the body in a more natural fashion, thereby improving drug therapy.

The means whereby the liver handles insulin illustrates the activity of this important target organ.

Insulin is a hormone which affects the metabolism of the animal as a whole. The most dramatic effect of this hormone is its ability to reduce the concentration of glucose in plasma. Ingested carbohydrate meals are normally digested to glucose in the gut and then absorbed into the portal circulation. The pancreas responds to carbohydrate in the gut with a release of insulin into the portal circulation. The portal vein carries the absorbed glucose and the released insulin to the liver. At the liver the insulin regulates the metabolism of glucose by the liver cells. By an unknown mechanism the liver retains most of the insulin but releases some to facilitate glucose utilization by muscle and adipose tissue. Reduction in blood glucose is due to the insulin effect on both liver and peripheral tissues. Thus, while the pancreas is the source of insulin within the organism, the liver is key to its normal utilization.

Diabetes mellitus is a generalized, chronic metabolic disorder manifesting itself in its fully developed form by hyperglycemia, glycosuria, increased protein breakdown, ketosis and acidosis. If the disease is prolonged, it is usually complicated by degenerative disease of the blood vessels, the retina, the kidneys and the nervous system. In diabetes mellitus, the pancreas either produces or releases insufficient insulin following a carbohydrate meal. This insulin deficiency results in an inability of most tissues to utilize the glucose which is in the blood. As a result, the blood glucose rises to abnormally high levels. When the blood glucose level exceeds the ability of the kidney to reabsorb glucose from the plasma ultrafiltrate, it appears in the urine. In addition, the cells of the body fail to metabolize other nutrients properly and growth is usually impaired. Lack of insulin to tissues eventually also results in abnormally high levels of toxic ketone metabolites in the blood. The final combined effect of these changes can be coma and death.

Insulin therapy for diabetes mellitus began in 1922. In current medical practice insulin is administered subcutaneously because the oral administration of the insulin is inefficient, presumably due to proteolysis. Subcutaneously administered insulin does produce a lowered level of blood glucose, primarily as a result of its action on muscle and fat tissue.

In the maintenance of the severely insulin-deficient diabetic patient, insulin administration is critical. However, insulin administration by injection can hardly be classified as a near normal state. Importantly, the anatomic arrangement of the pancreas in the normal individual is such that high levels of insulin secreted by the pancreas in response to oral glucose loads pass by way of the portal circulation to the liver before entering the peripheral circulation. By comparison, when insulin is administered subcutaneously to the diabetic patient, the peripheral tissue has first access to the hormone and may reduce the level of insulin presented to the liver and, in turn, reduces the effectiveness of the liver as a significant glucose regulating mechanism. Therefore, insulin administered by injection does not have the same physiological action as insulin released from the pancreas.

The present invention provides a means whereby insulin or other pharmacologically-active agents can be delivered preferentially to the liver in a human or lower animal.

The present invention also provides improved means for administering enzymes, vitamins and other drug agents, especially interferon, to humans and lower animals in need of such treatment.

BACKGROUND ART

The following articles comprise an overview of work in this area. Each of the publications contains citations to additional references.

EDTA has been encapsulated in liposomes and injected as a treatment for heavy metal poisoning. Tissue uptake of the EDTA in soft tissues such as the liver is said to increase some 20-fold over direct injection of non-encapsulated EDTA. Problems with liposome preparation and pulmonary embolisms are mentioned. Rahman, et al., *J. Lab. Clin. Med.* 83 (4), 640-7 (1974) and U.S. Pat. No. 3,932,657, issued Jan. 13, 1976, assigned to The U.S. Energy Research and Development Administration.

The oral administration of insulin by encapsulation within lecithin/cholesterol liposomes is reported in *FEBS Letters* 62, 1, 60-3 (1976) by Patel, et al. See also The Republic of South Africa Application for Patent Ser. No. 73/1850, which discloses and claims the use of various liposome-forming materials to encapsulate insulin for oral delivery.

Liposome materials containing a humectant and their use for moisturizing skin by topical application are disclosed in U.S. Pat. No. 3,957,971, issued May 18, 1976.

The U.S. Energy Research and Development Administration has filed U.S. Patent Application Ser. No. 513,210 (Oct. 19, 1974), now U.S. Pat. No. 3,993,754, which encompasses actinomycin D encapsulated in liposomes for cancer chemotherapy. This application has been laid open to the public as being available for licensing. A research report relative to the patent appears in the *Proceedings of The Society for Experimental Biology and Medicine* 146, 1173-76 (1974).

Belgian Pat. No. 830,629 (1975) discloses and claims immunologically active compositions characterized by an immunologically effective agent incorporated in a negatively charged liposome. Some of the agents thus encapsulated include virus antigens, bacterial antigens, and the like.

Liposomes comprising certain galactosyl lipids are described in *Immunochemistry*, Vol. 11, 475–81 (1974) by workers at the Walter Reed Army Institute of Research. Other work on galactosyl lipid membranes has been carried out at the Pasteur Institute (ibid. Vol. 13, 289–94) and elsewhere, as reported in *Biochimica et Biophysica Acta* 311, 531–44 (1973). These latter publications do not appear to report the preparation of liposomes from the membrane material.

U.S. Pat. No. 3,937,668, issued Feb. 10, 1976, discloses insulin encapsulated in albumin millimicrospheres.

Battelle Memorial Institute-International Division has disclosed a means for encapsulating various water-soluble drugs in liposomes using an ultrasonic vibration technique. German Offen. No. 2,532,317 (1974).

An entirely different class of encapsulating vesicles called "UFASOMES" have been prepared from Unsaturated Fatty Acids and are reported to closely resemble phospholipid liposomes in their structure and properties. Gebicki, et al., *Chem. Phys. Lipids* 16 (2), 142–60 (1976).

The *New England Journal of Medicine*, Sept. 23, 1976, pages 704–10 and Sept. 30, 1976, pages 765–70 comprises an extensive report on liposomes, their use in drugs, and contains multiple references to the types of drug agents encapsulated in liposomes.

A review article appearing in the *Journal of Lipid Research* 9, 310–18 (1968) discloses various general aspects about liposomes and their formation. Another article appearing in *Laboratory Investigation* 34, No. 3, 276, et. seq. (1976) discusses the entrapment of liposomes in the liver. The in vivo fate and distribution of synthetic lipid vesicles has been studied and reported in the *Proceedings of the National Academy of Sciences* 71, No. 9, 3487–91 (Sept. 1974). In this study, radioactive technetium was used to monitor the fate of the liposomes. Another study in tumor bearing mice appears in *Life Sciences* 17, 715–24.

The injection of drugs, including insulin, into rats to study the duration of intramuscular absorption is reported in *Chem. Pharm. Bull.* 23 (10) 2218–22 (1975).

J. Arehart-Treichel, *Science News*, Vol. 114, No. 4 (July 22, 1978) at page 60 reports that some workers have tagged liposomes with antibodies to help direct liposomal-packaged enzymes to appropriate target cells for the management of certain disease states.

A particularly relevant article with regard to the present invention is by Mauk and Gamble, *Proc. Natl. Acad. Sci. USA*, 76, No. 2, pp. 756-769, February, 1979, Biophysics. In that article, the authors report experiments relating to the work of Lunny and Ashwell (*Proc. Natl. Acad. Sci, USA*, 73, 341–343, 1976) that raised the possibility that surface carbohydrates may serve as determinants for recognition of liposomes by particular tissues. The work of Lunney and Ashwell describes a specific hepatic receptor capable of recognizing and binding galactose-terminated glycoproteins. However, the work of Mauk and Gamble shows that the presence of either fucose or galactose on the surface of the particular vesicles they studied causes "no statistically significant alteration in the tissue distribution of the vesicles."

Gregoriadis, *Biochemical Society Transactions*, Vol. 3 (1975) p. 613 reports the delivery of bleomycin and radioisotopes (but not insulin or interferon) to the liver using liposomes comprising asialofetuin. (Asialofetuin contains a galactosyl unit.) The work indicates that liver uptake over controls was enhanced, but the statistical significance of the data is unclear.

U.S. Pat. No. 4,016,100, issued Apr. 5, 1977, discloses a pharmaceutical composition which is prepared by dispersing a phospholipid in water, adding a medicament to the aqueous dispersion, freezing said aqueous dispersing to entrap the medicament in lipid spherules, and then thawing the frozen dispersion to give an aqueous suspension of the medicament entrapped in the lipid spherules.

U.S. Pat. No. 4,016,290, issued Apr. 5, 1977, discloses a method for transferring chelating agents across a cellular membrane by encapsulating the charged chelating agent within liposomes, which liposomes are taken up by the cells.

U.S. Pat. No. 4,078,052, issued Mar. 7, 1978, discloses unilamellar vesicles which encapsulate a drug.

The *Lancet*, June 29, 1974, pp. 1313–1316, discloses the possibility of using liposomes as carriers of drugs in patients with metastatic cancer.

Shipley, *Biochimica et Biophysica Acta* 311 (1973) 531–544 discloses the phase behavior in water of mono- and digalactosyl diglycerides. The phase behavior of glycolipids and phospholipids are compared and considered in terms of their respective roles in plant and animal cell membranes.

DISCLOSURE OF INVENTION

The present invention encompasses Lipid Membrane Structures for administering drugs, diagnostic agents, or the like, to a human or lower animal, comprising a mixture of a major portion of a polar lipid and a minor portion of a digalactosyl derivative having at least one fatty substituent.

The invention also encompasses compositions of matter comprising a first component which is a drug, diagnostic agent, or the like, said first component being encapsulated in or associated with a second component which comprises the aforesaid Lipid Membrane Structure which comprises a mixture of a major portion of a polar lipid and a minor portion of a digalactosyl derivative having at least one fatty substituent.

The invention also encompasses means for delivering a drug or radiodiagnostic agent to the hepatocytes of the liver of a human or lower animal by means of Lipid Membrane Structures of the herein-disclosed type.

The special advantage of the present invention resides in the discovery that the digalactosyl moiety targets the Lipid Membrane Structures preferentially to the hepatocytes of the liver. Thus, insulin can be delivered to the liver of the diabetic patient, where it is handled in a manner akin to that in the non-diabetic. The Lipid Membrane Structures can also be used to deliver other drugs and diagnostic agents to the liver as an aid in treatment of diseases involving that organ, itself.

The following are non-limiting examples of the kinds of materials which can be administered to humans and lower animals in Lipid Membrane Structures of the type disclosed herein:

1. Radionuclides, especially the radionuclides technetium-99m, thallium-201, indium-113m, indium-111, fluorine-18, strontium-85 and iodine-125;

2. Heavy metal chelators, especially the ethylenediaminetetraacetates and the diethylenetriaminepentaacetates;

3. Insulin, or insulin derivatives;

4. Anti-viral agents, especially those used in the treatment of hepatitis;

5. Interferon;

6. Hormones, e.g., estrogens (liver regeneration), glucagon, catecholamines;

7. Essential amino acids; and

8. Nucleotides (e.g., ATP) to enhance liver function.

Various other enzymes, drugs, vitamins and macromolecules such as those listed by Gregoriadis, *New England Journal of Medicine* 295 13 at 704–709 can also be administered to humans and lower animals using the Lipid Membrane Structures of this invention. Included among such materials are: Methotrexate, Bleomycin, Actinomycin D, and the like.

BEST MODE

The Lipid Membrane Structures used herein comprise a polar lipid and a digalactosyl derivative.

The most highly preferred polar lipid used in the practice of this invention is distearoyl lecithin. Natural lecithin (phosphatidyl choline; vitellin) comprises a mixture of the diglycerides of stearic, palmitic and oleic acids linked to the choline ester of phosphoric acid and is found in all living plants an animals. Lecithin has the structure:

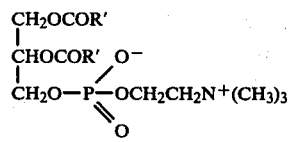

wherein each R'COO- substituent is a fatty acid residue.

The lecithin of commerce is predominantly soybean lecithin, obtained as a by-product in the manufacture of soybean oil: Stanley in K. S. Markley, *Soybeans* Vol. II (Interscience, New York, 1951) pp. 593–647. Soybean lecithin contains palmitic acid 11.7%, stearic 4.0%, palmitoleic 8.6%, oleic 9.8%, linoleic 55.0%, linolenic 4.0%, $C_{20}$ to $C_{22}$ acids (includes arachidonic) 5.5%. Synthesis of a mixed acid α-lecithin is disclosed by de Haas, van Deenen, *Tetrahedron Letters* 1960 (no. 9) 1. Synthetic L-α-(distearoyl)lecithin ("distearoyl lecithin") is manufactured commercially by hydrogenating egg yolk lecithin; L-α-(dipalmitoyl)lecithin is identical with a natural phosphatide of brain, lung and spleen.

The most highly preferred digalactosyl derivative used in the manner of the present invention is 1-O-[6-O-(α-D-galactopyranosyl)- β-D-galactopyranosyl]-2,3-di-O-acyl-D-glyceritol, conveniently named "Digalactosyl Diglyceride", abbreviated "DGDG." The DGDG is optionally, and preferably, hydrogenated in standard fashion ($H_2$ Pd-C) at the unsaturated linkages simply to decrease the chances of oxidation on storage. The physico/chemical characteristics of the "natural" DGDG are not otherwise affected. The term "DGDG" as used herein includes both the hydrogenated and unhydrogenated form.

DGDG occurs in nature and is reported to have the structure:

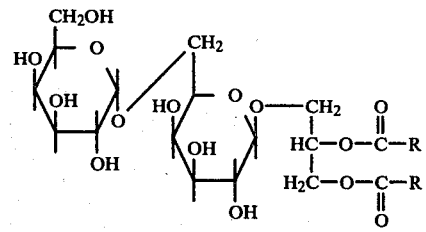

wherein each R substituent is in the $C_{15}$–$C_{17}$ chain range, ca. 20% palmitic, 9% oleic, 66% linoleic, the balance being stearic, linolenic and other minors. Myhre, *Canadian Journal of Chemistry* 46, 19, 3071–77 (1968), incorporated herein by reference.

The DGDG used in this invention was secured in the manner disclosed by Myhre, above. Russell-Miller American Beauty soft wheat flour (23 kg.) was suspended in ethanol (46 l) and the mixture was allowed to stand for several hours. The supernatant was withdrawn and filtered and the insoluble residue was extracted twice as before. The filtrates were evaporated to a syrup (215 g.).

In a typical run a portion of the ethanol extracted material (20–30 g.) from above was dissolved in chloroform (200 ml.) and applied to a column of silicic acid (100 mesh) (3.6×88 cm.) which had been washed previously, first with chloroform-methanol (50:50 v/v) and then with chloroform. The column was irrigated with chloroform followed by mixtures of chloroform and methanol similar to the method of Carter et al., *J. Lipid Res.* 2, 215 (1961). Each fraction collected amounted to ca. 15–20 mls. Appropriate fractions were combined, evaporated and the residues were stored at 0° C. until used. The fractions collected were as follows (see Myhre, above, for complete analyses of individual fractions).

TABLE I

| Fraction | Solvent CHCl₃:MeOH (v/v) | Components |
|---|---|---|
| 1–50 | 100:0 | Lipid (discard) |
| 51–70 | 100:0 | Glyceritols (disc.) |
| 120–150 | 98:2 | Glucopyranosides (disc.) |
| 160–180 | 96:4 | Glyceritols (disc.) |
| 181–210 | 94:6 | Glyceritols (disc.) |
| 301–450 | 92:8; 90:10 | DGDG (retain) |

LMS MANUFACTURE

The following procedure illustrates the preparation of Lipid Membrane Structures (LMS) containing insulin. The same techniques can be used to prepare LMS containing other drug agents. In this procedure, the term DSL refers to distearoyl lecithin and the term DGDG refers to digalactosyl diglyceride prepared in the manner of Myhre, above.

A glass syringe was fitted with a piece of polypropylene tubing to facilitate aliquoting the DGDG stock solution (below). Likewise, a 5.0 ml. glass syringe was fitted with a piece of 1 mm. ID polypropylene tubing to aliquot the DSL stock solution (below). A 10.0 ml. glass syringe fitted with an 18 gauge needle was used throughout the procedure to aliquot 8.0 ml. of commercial insulin stock solution. 6.0 ml. of stock DSL and 2.0 ml. of stock DGDG were transferred to a 50 ml. Erlenmeyer weighing flask with very gentle mixing under dry nitrogen. The flask was then situated in a 55° C. water bath while nitrogen was blown over the sample to dry the lipid components.

The sample flask was then placed on a Buchi Roto-evaporator under house vacuum and rotated slowly for 15 minutes while the temperature was maintained at 65° C. with a water bath. The dried sample was then flushed with nitrogen and 12.0 ml. of insulin stock solution (below) was added. The flask was then positioned in a micro tip or, preferably, a cup horn sonicator reservoir (Heat Systems Ultrasonics) such that the bottom surface of the flask maintained a 1/16 inch clearance from the radiating surface of the horn.

In order to provide for continuous monitoring of the reaction temperature, a thermistor probe was inserted in the aqueous phase. A glass stopper was then inserted in the neck of the flask and wrapped securely with Parafilm to seal and prevent evaporation of the aqueous components during sonication. The temperature of the reaction mixture was maintained at a constant 60° C.±0.5° C. for a 45-minute period. Temperature control was achieved using a Lauda K-2/R circulating water bath. In addition, the bath level in the cup horn reservoir was maintained 1¼ inches above the radiating surface of the horn to facilitate temperature control in the reaction media.

The power output needed for sonication was derived from a model #350 power amplifier from Heat Systems Ultrasonic. The power output control was set at position #3 to provide power output equivalent to 40%–60% of amplifier capacity. The electrical energy delivered to the horn was transduced to provide the ultrasonic energy needed for sonication.

Following sonication the condensed vapor and lipid components were mixed. The sample was then placed on a Buchi Roto-evaporator and annealed with slow turning in a 65° C. water bath for 1 hour. Immediately following this initial annealing the sample was incubated at room temperature for ½ hour. A second annealing, identical to the first, followed the incubation period.

In order to free the insulin-containing LMS from external insulin a minimum of five washes were conducted using a Beckman L-5 ultracentrifuge equipped with an S.W. 60 head. The insulin-LMS preparation was transferred to a 3.0 ml. capacity polyallomer centrifuge tube and centrifuged at 55,000 rpm for 2 hours.

Stock solutions used in the foregoing process were as follows. Stock DSL comprises 57.69 mg. of DSL per ml. of a 2:1 v/v CHCl$_3$/methanol. Stock DGDG comprises 6.926 mg./ml. CHCl$_3$/methanol (2:1 v/v). Insulin stock solution comprising: 8.0 ml Lilly Insulin/100 units per ml./0.2 wt.% phenol and 4.0 Iodine-125 Insulin, Amersham, containing 0.5% w/w albumin and 0.05% thimerosal.

In an alternate mode in the above process which is preferred for securing higher concentrations of insulin associated with the LMS, 100 mg crystalline insulin is added directly to the mixture of stock solutions of DSL and DGDG. The suspension of crystalline insulin is sonicated (ca. 30 sec./room temp.) with the cup horn sonication to disperse the insulin. Following vacuum evaporation of solvent, as disclosed, the dried sample is treated with the insulin stock solution, sonicated, etc., as described above.

It will be appreciated that the foregoing procedures can be modified by replacing the insulin solution with a solution of other drug agent of choice to secure LMS comprising such other drug agent.

LMS containing various percentages of DGDG, or without DGDG for use in control experiments, can also be prepared using the foregoing sonication technique.

In like manner, various DGDG-containing LMS can be prepared by sonicating DGDG with glycerides/lipids other than DSL.

Other general procedures for preparing LMS without DGDG are disclosed in U.S. Pat. No. 4,016,290, issued Apr. 5, 1977, incorporated herein by reference. Such procedures can also be used herein by adding the appropriate level of DGDG to the art-disclosed polar lipids and proceeding in the manner described in the referenced patent.

The stability of the LMS herein is substantially enhanced by suspension in an aqueous electrolyte solution. This is presumably due to osmotic pressure considerations. Pharmaceutically-acceptable electrolytes such as KCl and NaCl (preferred) are useful for this purpose. Physiologic saline (commercial) can be used. The resulting LMS suspensions in aqueous electrolyte are suitable for direct use in the manner disclosed.

Insulin LMS prepared in the foregoing manner can be "sized" by liquid chromatography on Sepharose 2b (Pharmacia), using standard techniques. For example, the sonicated insulin LMS is centrifuged at 100,000 X g for 1 hour to remove large particle size vesicles, aggregates and undefined structures. Chromatography of the remaining material on Sepharose 2b provides insulin vesicle in the 750 Angstrom—3000 Angstrom range. Additionally, insulin not associated with the LMS is desirably removed from the final composition by this procedure. If desired, larger vesicles (greater than ca. 4000 A) can be separated from smaller vesicles using hydrodynamic chromatography.

ANIMAL TESTING

Animal tests were run to demonstrate the effectiveness of the insulin-LMS with DGDG for controlling glucose. The studies also demonstrated that insulin-LMS without DGDG are only about as effective as insulin in this regard. The studies also demonstrated that the effect of insulin-LMS with DGDG in the diabetic animal is very much like that obtained through natural body mechanisms in a healthy animal. In contrast, insulin and insulin-LMS without DGDG yield dose responses which are quite different from normal.

STUDY I

The insulin used in this study was regular pork injectable insulin, 100 units/cc. (Eli Lilly, Indianapolis). The digalactosyl diglyceride (DGDG) and distearoyl lecithin (DSL) were as disclosed above. Four preparations were tested: 100% DSL+insulin; 96% DSL+4% DGDG+insulin; 96% DSL+4% DGDG+saline; and insulin. The LMS with insulin or saline, with and without DGDG, were prepared by sonication.

Briefly, the four compositions were separately administered to animals via catheter directly into the duodenum. The animals had been fasted 20 hours prior to administration.

The results from the study indicated that animals receiving insulin-LMS compositions with DGDG exhibited a significant hypoglycemic effect when compared with the insulin-treated controls. Indeed, insulin, LMS+DGDG+saline, and LMS+insulin without DGDG did not produce significant hypoglycemia. Glucose values for insulin-LMS with DGDG were significantly different from the regular insulin treatment at 50, 75, 90, 105 and 120 minutes. Glucose values for insulin-LMS with DGDG were significantly different from insulin-LMS without DGDG treatment at 75, 105 and 120 minutes, and also for saline LMS+DGDG at 105 minutes.

As disclosed above, other workers have shown that lipid liposome insulin preparations can induce hypoglycemia in diabetic rats. Doses used by those workers were in the range of 50-100 units of insulin/kg., and hypoglycemia effects were observed only in diabetic rats but not in intact animals. In the present study, the only group which showed significant hypoglycemia was the insulin-LMS with DGDG group. Doses in this study were estimated by ultraviolet absorption to be ca. 3 units/kg.

STUDY II

A second study was carried out in substantially the same manner as Study I, but with a lower dose of insulin (0.35 units/kg. of body weight). The LMS were prepared by sonication, with annealing at 67° C. for 60 minutes.

The results from Study II confirmed that low doses (0.35 u/kg. body weight) of DSL/DGDG-insulin-LMS, when administered intraduodenally to fasted, intact and awake animals produce a biologically and statistically significant hypoglycemic response 45-75 minutes post dosing. Moreover, DSL-insulin-LMS which did not contain the DGDG had no effect on plasma glucose. Finally, regular insulin and saline administered intraduodenally had no effect on plasma glucose values in Study II.

STUDY III

In this study, insulin was administered via the duodenum to diabetic animals so that any insulin that was absorbed would be presented to the liver via the portal circulation, thereby mimicking the normal pattern of insulin delivery. Three forms of insulin were tested: regular insulin, insulin in DSL LMS structures without DGDG and insulin in DSL LMS structures containing DGDG.

Animals were made diabetic by administering intravenously 50 mg. Alloxan/kg. body weight and 30 mg. Streptozotocin/kg. body weight to the fasted animals. Insulin administration was withdrawn from each animal 48 hours before catheterization. Six days after induction of diabetes, studies were begun following the general technique of Studies I and II, herein.

Insulin used in the study was regular pork insulin for injection (Lilly). The LMS preparations were as in Studies I and II.

Three groups of animals were used in the study; the animals were anesthetized and catheters were placed surgically. Blood for the determination of plasma glucose and insulin concentrations was collected at 0, 15, 30, 60, 75, 90, 120 and 150 minutes. At 0 time, each test animal received a 10 ml. infusion of saline, 37° C., into the duodenum. Immediately after the 60 minute blood samples were collected, the animals in Group 1 received 10 units insulin/kg. body weight as regular insulin injected into the duodenum; the animals the Group 2 received 10 units/kg. body weight of LMS insulin without DGDG; and Group 3 received 10 units insulin/kg. body weight in LMS containing 4% DGDG.

In Study III the regular insulin was shown to have no effect either on circulating levels of plasma glucose or on the uptake of glucose by the liver. Insulin administered in LMS without DGDG had no effect on plasma glucose, nor did it restore hepatic glucose retention utilization in the diabetic animals. In contrast, animals that received insulin in LMS containing DGDG introduodenally did show a significant fall in plasma glucose in two of three test animals. The decline in glucose was greatest 90 minutes following administration, and the fall began at 15 minutes. An increase in the hepatic retention of glucose was demonstrable at 15 minutes and was maximum at 60 minutes, then returned towards base line levels at 90 minutes. The uptake of glucose by hepatic tissue could have accounted for the fall in plasma glucose.

Based on the results of Study III, it was concluded that regular insulin and the insulin administered in LMS without added DGDG had no effect on either plasma glucose or hepatic or peripheral retention of glucose. In contrast, the same dosage of insulin in LMS containing DGDG did induce a hypoglycemic response in the peripheral plasma. Moreover, it was demonstrated by calculation of glucose differences (portal vein minus hepatic vein) that there was an increased hepatic uptake of glucose in animals which had received the insulin LMS with DGDG.

STUDY IV

In normal control animals it was found that the liver changes from a condition of glucose output in the basal fasting state to one of uptake when it is presented with infused glucose. This is the kind of response expected in an individual whose pancreas and liver are functioning normally. Control diabetic animals, on the other hand, lose this ability to take up glucose by the liver and they maintain a net output of glucose throughout experiments even though large amounts of glucose are being infused into the portal system. Therefore, the diabetic faces the problem that even though large amounts of glucose are ingested via the digestive tract and the portal blood system, the liver continues to make even more glucose instead of storing glucose that is ingested.

In this study insulin in lipid membrane structures (96% DSL and 4% DGDG) was infused into the jugular vein of diabetic dogs. During this interval the same dogs were infused with glucose via the mesenteric vein (portal system) at a rate of 0.5 grams glucose/kg. body weight/hour. The animals were prepared in such a way that the liver was isolated for metabolic studies. The hepatic artery was ligated so that the only incoming blood came in via the portal system and exited via the hepatic vein. Catheters were placed into the hilus of the liver in the portal vein so that ingoing blood could be sampled at that point, and another catheter was placed in the hepatic vein so that blood leaving the liver could be sampled. Hepatic blood flows were measured by infusing a bolus of indocyanine green into a mesenteric vein. The appearance of the indocyanine green was detected by a constant withdrawal of blood from the hepatic vein and analyzed by a Gilford Cardiac Output system which computes the rate of flow. Therefore, the system was one in which concentrations of glucose could be determined going into and coming out of the liver, and the flow rate of the blood was also known. The calculation of concentration of glucose multiplied by the flow rate gives the absolute amount of glucose either taken up by the liver or released by the liver.

Insulin was infused into the diabetic dogs via either the jugular vein or the portal vein. The dose responses for the effect of insulin upon the hepatic retention of glucose phenomenon were determined. It was shown that the portally-infused insulin could produce a normal hepatic uptake of glucose at a dose of 1.0 milliunits of insulin infused per minute/kg. body weight, whereas to accomplish the same effect insulin infused into the jugular vein required a dose of 6.25 milliunits/kg. body weight/minute. A jugular dose of 2.5 milliunits/kg. body weight was ineffective in converting the liver from a state of glucose output to a state of glucose uptake.

The insulin/lipid membrane structure containing the Digalactosyl Diglyceride (4% w/w) was active when infused in the jugular vein at a dose range of 0.026 to 0.4 milliunits insulin/kg. body weight/minute. The dramatic reversal of the hepatic system from glucose output to glucose uptake at this low dose is consistent with the position that the insulin in the LMS with DGDG is directed to the hepatocytes, which release the insulin in some manner, which, in turn, causes a conversion from a state of glucose output to a state of glucose uptake.

Based on the results of Study IV, it was concluded that the liver-directed LMS system with the DGDG provides the liver with an adequate dose of insulin to convert it to a hepatic storage of glucose mode at a much lower dose than is seen with the regular insulin. The DSL/DGDG LMS thus allows the animal to have a normal metabolic pattern for handling ingested glucose loads, as compared with the inability of regularly administered (without the DSL/DGDG LMS) insulin to cause this effect.

INDUSTRIAL APPLICABILITY

In general, the LMS comprise from about 90% to about 99.9% by weight of the polar lipid and from about 0.1% to about 10% by weight of the digalactosyl derivative. LMS which comprise from about 95% to about 99% by weight of the polar lipid and from about 1% to about 5% by weight of the digalactosyl derivative are highly preferred.

The following are typical polar lipids useful in the practice of this invention: dicetyl phosphate, stearylamine, phosphatidic acid, dipalmitoyl phosphatidyl choline, dimyristoyl phosphatidyl choline, sphingomyelin, phosphatidyl inositol, cardiolipin, lysophosphatidyl choline, phosphatidyl ethanolamine, gangliosides, phosphatidyl serine, and mixtures thereof. These polar lipids are available using art-disclosed methods (see references cited in Gregoriadis, above). Cholesterol is a polar lipid often used in combination with art-disclosed polar lipids to stabilize the walls of vesicles and liposomes, and can optionally be used in the same manner with the LMS of this invention.

The preferred polar lipids for preparing the LMS comprise the dialkanoyl lecithins wherein the alkanoyl groups each contain from about 12 to about 20 carbon atoms. LMS wherein the alkanoyl groups are selected from palmitoyl and stearoyl, especially distearoyl lecithin, are most preferred.

LMS wherein the digalactosyl derivative is a fatty glyceride digalactosyl derivative characterized by at least one fatty substituent having a chain length in the range from about $C_{12}$ to about $C_{20}$, especially those where the digalactosyl derivative is a diglyceride, are highly preferred.

LMS wherein the digalactosyl derivative is Digalactosyl Diglyceride of the formula disclosed above (DGDG) are most highly preferred for directing drugs, radionuclides, and the like to the liver in humans and lower animals.

Lipid Membrane Structures which comprise a mixture of from about 94% to about 97% by weight of distearoyl lecithin and from about 3% to about 6% by weight of Digalactosyl Diglyceride are the most highly preferred carriers for drugs, and the like. Such LMS which comprise, as an additional ingredient, a stabilizing amount (usually about 0.5% to about 3%) of cholesterol are also useful for injection into humans and lower animals as a drug carrier.

The foregoing LMS are designed for use with a component which is a drug, radiodiagnostic agent, or the like, said component being encapsulated in or associated with the LMS. Such combinations of LMS-drug, LMS-diagnostic agent, etc., are preferably used in a liquid carrier (usually sterile, pyrogen-free aqueous saline) suitable for injection into a human or lower animal.

Highly preferred compositions of the type disclosed herein comprise insulin in combination with Lipid Membrane Structures which comprise a mixture of from about 94% to about 97% by weight of distearoyl lecithin and from about 3% to about 6% by weight of Digalactosyl Diglyceride, said Lipid Membrane Structures being, most preferably, dispersed in a liquid carrier (e.g. water) suitable for injection into a human or lower animal.

The preferred procedure for preparing LMS containing drugs, or the like, is disclosed in detail hereinabove for preparing the insulin-LMS+DGDG, and this procedure is equally useful for preparing LMS with other drugs and using other polar lipids. Such LMS typically comprise substantially spherical vesicles (or liposomes) having an average particle diameter of ca. 10 microns ($\mu$) and below, and are suitable for injection into humans and lower animals. The preferred average particle size range is from about 250 A to about 3000 A, most preferably 750 A to 3000 A. Typical concentrations of drugs, radionuclides, and the like, prepared in this manner and suitable for use in humans and lower animals are listed in Table II.

TABLE II

| Agent Type | Amount per gram of neat* LMS |
| --- | --- |
| Chelators | 0.01 mg. → 1000 mg. |
| Insulin and Insulin Derivatives | 1 unit → 1000 units |
| Vitamins | 20 IU → 4000 IU |
| Radionuclides** | 0.001 mg. → 100 mg. |
| Antineoplastics | 0.001 mg. → 100 mg. |
| Antivirals | 0.01 mg. → 1000 mg. |

*"Neat" LMS denotes the LMS without added carriers such as water.
**Amounts will vary with intended use and radiation intensity. For radiodiagnosis, 20 → 20,000 $\mu$Ci are typical use levels. For radiotherapy, usage levels are ca. 10 → 100-fold higher, depending on the disease state.

The following examples further illustrate the practice of this invention, but are not intended to be limiting thereof. It will be appreciated that the selection of actual amounts of specific LMS/drug agents to be administered to any individual patient (human or animal) will fall within the discretion of the attending physician (or veterinarian) and will be prescribed in a manner commensurate with the appropriate risk:benefit ratio for that particular patient. Appropriate dosages will depend on the patient's age, weight, sex, stage of disease and like factors uniquely within the purview of the attending physician. As a general rule, the amount of specific drug administered in conjunction with the LMS disclosed herein will be in the range of 20% to 100% of that administered without the LMS. The LMS compositions can be administered via the G.I. tract, parenterally, e.g., by i.v. infusion, and by injection.

EXAMPLE I

LMS containing $^{99m}$Tc are prepared in the manner disclosed above, and comprise the following.

| Ingredient | Amount/g. of LMS Composition |
|---|---|
| DGDG | 0.04 g. |
| DSL | 0.90 g. |
| $^{99m}$Tc* | 0.06 g. |

*As $^{99m}$TcO$_4^\ominus$ to provide ca. 1000 μCi per g. of LMS.

The ratioactive LMS composition of Example I is suspended in sterile, pyrogen-free saline (1 LMS:10 saline by weight). Three mls. of the suspension are injected intravenously into a patient ca. one hour after preparation. The patient is rested for a period of one hour and then liver scan photos are taken using standard techniques. The photos show excellent liver detail, without substantial interference from surrounding soft tissues.

The composition of Example I is modified by substituting the following polar lipids for the DSL, respectively: diacetyl phosphate, stearylamine, phosphatidic acid, dipalmitoyl phosphatidyl choline, dimyristoyl phosphatidyl choline, sphingomyelin, phosphatidyl inositol, cardiolipin, lysophosphatidyl choline, phosphatidyl ethanolamine, gangliosides, phosphatidyl serine, and mixtures thereof. Excellent liver scans are secured.

Radioactive LMS compositions are prepared in like fashion using Tl-201; In-113m; In-111; F-18; Sr-85 and I-125, respectively.

EXAMPLE II

LMS containing heavy metal chelators are prepared in the manner disclosed above, and comprise the following.

| Ingredient | Amount/g. of LMS |
|---|---|
| DGDG | 0.03 g. |
| DSL | 0.87 g. |
| Sodium ethylenediaminetetraacetate | 0.10 g. |

The composition of Example II is suspended in sterile, pyrogen-free saline (1:1) and is administered intravenously to an animal (80 kg. body weight) suffering from lead poisoning. A total of 10 grams of the suspension are perfused per day. The procedure is repeated once daily for a period of seven days. The feces and urine of the animal are monitored over this seven-day treatment period. At the end of the period, substantially all lead residues are removed from the liver of the animal.

The composition of Example II is modified by replacing the NaEDTA with an equivalent amount of the sodium salt of ethylenetriaminepentaacetate, sodium citrate, and sodium ethane-1-hydroxy-1,1-diphosphonate, respectively, and equivalent results are secured.

The composition of Example II is ingested orally to secure removal of lead.

EXAMPLE III

LMS containing gamma globulin are prepared in the manner disclosed above and administered to a subject which has come into contact with a patient suffering from viral hepatitis. A dosage of LMS comprising about 0.02 ml./kg. of gamma globulin suffices to provide at least transient protection against hepatitis A.

Chronic hepatitis is treated in the manner of this invention by injecting an LMS suspension made in the manner of Example I containing up to 100 mg. azathioprine. Administration of the azathioprine-LMS by injection over a period of one month by the physician provides an effective means for managing chronic active hepatitis.

The azathioprine-LMS of Example III are administered orally with good results.

EXAMPLE IV

The LMS composition of Example I is modified by replacing the Tc radionuclide with 5-fluorouracil, Actinomycin D, and Methotrexate, respectively. Excellent liver hepatocyte targeting is secured.

EXAMPLE V

Vitamin D (4000 IU) is encapsulated in sonicated DSL-DGDG-cholesterol (96%:3%:1%) Lipid Membrane Structures and is specifically directed to the liver when administered i.v. in the manner disclosed herein.

EXAMPLE VI

Interferon produced from human leukocyte cultures is incorporated into DSL-DGDG Lipid Membrane Structures, as follows.

Interferon can be secured by various procedures: Green, et al., Science 164, 1415, 1969; Wheeloch, Science 149, 310, 1965; Richmond, Archiv fur die Gesamte Virusforshung 27, 282, 1969; and Friedman, et al., Proc. Soc. Exptl. Biol. Med. 125, 901; 1967. The following, preferred, procedure is fully described in "The Production and Use of Interferon for the Treatment and Prevention of Human Virus Infections" May, 1973, published by The Tissue Culture Association, 1211 Parklawn Drive, Rockville, Md. 20852. The method reported consists of the following steps. (The original paper can be referred to for exact details.)

1. Collection and pooling of "buffy coats" in 0.4% ethylenediaminetetraacetate (EDTA), pH 7.2.
2. Storage overnight at 4° C.
3. Treatment with 10 volumes of 0.83% NH$_4$Cl, 10 min, 4° C.
4. Centrifugation in a MSE 300 basket centrifuge, 1200 rpm. 500 ml per min.
5. Resuspension of cells in phosphate buffered saline (PBS) containing 0.5% EDTA and 25 μg per ml of neomycin.
6. Retreatment with NH$_4$Cl as above.
7. Resuspension of cells in Eagle's minimum essential medium (without phosphate buffer) supplemented with (NH$_4$)$_2$SO$_4$-treated human serum (5) at 4%, 3 mg per ml of tricine and 25 μg per ml of neomycin.
8. Adjustment of cell concentration to 10$^7$ per ml with the above medium.
9. Incubation of cells in 2 to 6 liter round flasks in water bath at 37.5° C. on magnetic stirrer. The flasks have at least 50% air space and are covered with foil.
10. Addition of 100 units per ml of leukocyte interferon.

11. Addition of 100 hemagglutinating (HA) units per ml of Sendai virus 2 hr later.

12. Incubation for 20 hr at 37.5° C.

13. Centrifugation at 2000 rpm for 40 min. The supernatant fluid is the crude interferon.

The continuous flow centrifuge permits treatment of 140 to 210 buffy coats per day. The continuous presence of serum or casein in the medium is necessary for optimum yields.

Following the LMS Manufacture Procedure disclosed above, substantially spherical (avg. size range 250 A to about 3000 A) vesicles containing interferon prepared in the foregoing manner are manufactured. The walls of the vesicles comprise ca. 96% DSL and ca. 4% DGDG. Typical interferon/vesicle preparations suitable for administration to humans, especially humans in need of treatment for viral hepatitis, comprise from about 10,000 to about 1,000,000 units of interferon per mg. of the vesicle carrier spheroids.

In an alternative mode, the DSL used to manufacture the vesicles of Example VI is replaced by an equivalent amount of dipalmitoyl phosphatidyl choline, stearyl amine and sphingomyelin, respectively. The presence of the digalactosyl moiety in the walls of the vesicles "targets" the vesicles to the hepatocytes.

I claim:

1. A composition of matter for internal administration in the therapeutic treatment of a human or animal comprising:
   (A) a first component which is a drug or diagnostic agent, said first component being encapsulated in or associated with;
   (B) a second component which comprises lipid membrane structures in the form of vesicles or liposomes, having an average particle diameter of between about 250 Angstroms and about 3000 Angstroms, which comprise a mixture of a major portion of a polar lipid and a minor portion of a digalactosyl derivative having at least one fatty substituent.

2. A composition according to claim 1 comprising from about 90% to about 99.5% by weight of the polar lipid and from about 0.5% to about 10% by weight of the digalactosyl derivative.

3. A composition according to claim 2 which comprises from about 95% to about 99% by weight of the polar lipid and from about 1% to about 5% by weight of the digalactosyl derivative.

4. A composition according to claim 1 wherein the polar lipid comprises a dialkanoyl lecithin wherein the alkanoyl groups each contain from about 12 to about 20 carbon atoms.

5. A composition according to claim 4 wherein the alkanoyl groups are selected from the group consisting of palmitoyl and stearoyl.

6. A composition according to claim 5 wherein the polar lipid is distearoyl lecithin.

7. A composition according to claim 1 wherein the digalactosyl derivative is a fatty glyceride digalactosyl derivative characterized by at least one fatty substituent having a chain length in the range from about $C_{12}$ to about $C_{20}$.

8. A composition according to claim 7 wherein the digalactosyl derivative is Digalactosyl Diglyceride.

9. A composition according to claim 1 wherein the Lipid Membrane Structures comprise a mixture of from about 94% to about 97% by weight of distearoyl lecithin and from about 3% to about 6% by weight of Digalactosyl Diglyceride.

10. A composition according to claim 9 wherein said vesicles or liposomes are in a size range of from about 750 Angstroms to about 3000 Angstroms.

11. A composition according to claim 1 or 9 in a liquid electrolyte-containing carrier suitable for injection into a human or lower animal.

12. A composition according to claim 1 or 9 which comprises, as an additional ingredient in the Lipid Membrane Structures, a stabilizing amount of cholesterol.

13. A composition according to claims 1, 8, 9 or 10 wherein said first component comprises a radionuclide.

14. A composition according to claim 13 wherein said radionuclide is selected from the group consisting of technetium-99m, thallium-201, indium-113m, indium-111, fluorine-18, strontium-85 and iodine-125.

15. A composition according to claim 1, 8, 9 or 10 wherein said first component is a heavy metal chelator.

16. A composition according to claim 15 wherein said heavy metal chelator is selected from the group consisting of the ethylenediaminetetraacetates and the diethylenetriaminepentaacetates.

17. A composition according to claim 1 wherein said first component comprises insulin, or an insulin derivative.

18. An insulin composition according to claim 17 comprising from about 90% to about 99.9% by weight of the polar lipid and from about 0.1% to about 10% by weight of the digalactosyl derivative.

19. An insulin composition according to claim 18 which comprises from about 95% to about 99% by weight of the polar lipid and from about 1% to about 5% by weight of the digalactosyl derivative.

20. An insulin composition according to claim 17 wherein the polar lipid comprises a dialkanoyl lecithin wherein the alkanoyl groups each contain from about 12 to about 20 carbon atoms.

21. An insulin composition according to claim 20 wherein the alkanoyl groups are selected from the groups consisting of palmitoyl and stearoyl.

22. An insulin composition according to claim 21 wherein the polar lipid is distearoyl lecithin.

23. An insulin composition according to claim 17 wherein the digalactosyl derivative is a fatty glyceride digalactosyl derivative characterized by at least one fatty substituent having a chain length in the range from about $C_{12}$ to about $C_{20}$.

24. An insulin composition according to claim 23 wherein the digalactosyl derivative is Digalactosyl Diglyceride.

25. An insulin composition according to claim 17 wherein the Lipid Membrane Structures comprise a mixture of from about 94% by weight of distearoyl lecithin and from about 3% to about 6% by weight of Digalactosyl Diglyceride.

26. An insulin composition according to claim 25 wherein said vesicles or liposomes are in a size range of from about 750 Angstroms to about 3000 Angstroms.

27. An insulin composition according to claim 17 25 or 26 dispersed in a liquid electrolyte-containing carrier suitable for injection into a human or lower animal.

28. An insulin composition according to claim 17 or 26 which comprises, as an additional ingredient, a stabilizing amount of cholesterol.

29. A composition according to claim 1 wherein said first component comprises interferon.

30. An interferon composition according to claim 29 comprising from about 90% to about 99.9% by weight of the polar lipid and from about 0.1% to about 10% by weight of the digalactosyl derivative.

31. An interferon composition according to claim 30 which comprises from about 95% to about to about 99% by weight of the polar lipid and from about 1% to about 5% by weight of the digalactosyl derivative.

32. An interferon composition according to claim 29 wherein the polar lipid comprises a dialkanoyl lecithin wherein the alkanoyl groups each contain from about 12 to about 20 carbon atoms.

33. An interferon composition according to claim 32 wherein the alkanoyl groups are selected from the group consisting of palmitoyl and stearoyl.

34. An interferon composition according to claim 33 wherein the polar lipid is distearoyl lecithin.

35. An interferon composition according to claim 29 wherein the digalactosyl derivative is a fatty glyceride digalactosyl derivative characterized by at least one fatty substituent having a chain length in the range from about $C_{12}$ to about $C_{20}$.

36. An interferon composition according to claim 35 wherein the digalactosyl derivative is Digalactosyl Diglyceride.

37. An interferon composition according to claim 29 wherein the Lipid Membrane Structures comprise a mixture of from about 94% to about 97% by weight of distearoyl lecithin and from about 3% to about 6% by weight of Digalactosyl Diglyceride.

38. An interferon composition according to claim 37 wherein said vesicles or liposomes are in a size range of from about 750 Angstroms to about 3000 Angstroms.

39. An interferon composition according to claim 29, 37 or 38 dispersed in a liquid electrolyte-containing carrier suitable for injection into a human or lower animal.

40. An interferon composition according to claim 29 or 37 which comprises, as an additional ingredient, a stabilizing amount of cholesterol.

* * * * *